United States Patent
Klotzer

(10) Patent No.: US 9,407,464 B2
(45) Date of Patent: Aug. 2, 2016

(54) SYSTEMS AND METHODS FOR AN APPLICATION MESSAGING INTEGRATION FRAMEWORK

(75) Inventor: Jason Dieter Klotzer, Yonkers, NY (US)

(73) Assignee: General Electric Company, Schenectady, NY (US)

( * ) Notice: Subject to any disclaimer, the term of this patent is extended or adjusted under 35 U.S.C. 154(b) by 614 days.

(21) Appl. No.: 13/362,084

(22) Filed: Jan. 31, 2012

(65) Prior Publication Data

US 2013/0132490 A1    May 23, 2013

Related U.S. Application Data

(60) Provisional application No. 61/563,226, filed on Nov. 23, 2011.

(51) Int. Cl.
  *G06F 15/16*    (2006.01)
  *H04L 12/64*    (2006.01)
  *G06F 19/00*    (2011.01)

(52) U.S. Cl.
  CPC ............ *H04L 12/6418* (2013.01); *G06F 19/32* (2013.01)

(58) Field of Classification Search
  CPC .......... H04L 67/10; G06G 15/16; G06F 9/44; G06F 9/54–9/548; G06F 3/048; G06F 19/30; G06F 19/32; G06F 19/321; G06F 19/322; G06F 8/36; G06F 8/38
  USPC ......................................................... 709/206
  See application file for complete search history.

(56) References Cited

U.S. PATENT DOCUMENTS

| | | | |
|---|---|---|---|
| 6,401,138 B1 * | 6/2002 | Judge et al. | 719/328 |
| 2005/0065423 A1 * | 3/2005 | Owen | G06T 15/08 600/407 |
| 2006/0010452 A1 * | 1/2006 | Sattler et al. | 719/313 |
| 2008/0059433 A1 * | 3/2008 | Callan et al. | 707/3 |
| 2008/0209348 A1 * | 8/2008 | Grechanik et al. | 715/762 |
| 2011/0078625 A1 * | 3/2011 | Mumford et al. | 715/804 |
| 2012/0130734 A1 * | 5/2012 | White | 705/2 |
| 2012/0253848 A1 * | 10/2012 | Gazula | 705/3 |
| 2013/0091513 A1 * | 4/2013 | Underdal | G06F 9/4843 719/328 |

* cited by examiner

*Primary Examiner* — Brian J Gillis
*Assistant Examiner* — Austin Moreau
(74) *Attorney, Agent, or Firm* — Hanley, Flight and Zimmerman, LLC

(57) ABSTRACT

Methods, systems, and computer-readable media are provided for an application messaging integration framework. An example method includes receiving a user input at a first clinical viewer via an integrated interface. The example method includes sending a message based on the input to a second clinical viewer via an application and messaging integrator. The application and messaging integrator is created to facilitate communication between the first and second clinical viewers. The example method includes updating information at the second clinical viewer based on the message. The example method includes displaying the updated information at the second clinical viewer via the integrated interface.

16 Claims, 15 Drawing Sheets

SYSTEMS AND METHODS FOR AN APPLICATION MESSAGING INTEGRATION FRAMEWORK

RELATED APPLICATIONS

This patent claims priority to U.S. Provisional Application Ser. No. 61/563,226, entitled "Systems and Methods for an Application Messaging Integration Framework," which was filed on Nov. 23, 2011 and is hereby incorporated herein by reference in its entirety.

FEDERALLY SPONSORED RESEARCH OR DEVELOPMENT

[Not Applicable]

MICROFICHE/COPYRIGHT REFERENCE

[Not Applicable]

BACKGROUND

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during and/or after surgery, medical personnel may access patient information, such as images of a patient's anatomy, which are stored in a medical information system. Radiologist and/or other clinicians may review stored images and/or other information, for example.

Using a PACS and/or other workstation, a clinician, such as a radiologist, may perform a variety of activities, such as an image reading, to facilitate a clinical workflow. A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools. For example, a radiologist or cardiologist typically looks into other systems such as laboratory information, electronic medical records, and healthcare information when reading examination results.

PACS were initially used as an information infrastructure supporting storage, distribution, and diagnostic reading of images acquired in the course of medical examinations. As PACS developed and became capable of accommodating vast volumes of information and its secure access, PACS began to expand into the information-oriented business and professional areas of diagnostic and general healthcare enterprises. For various reasons, including but not limited to a natural tendency of having one information technology (IT) department, one server room, and one data archive/backup for all departments in healthcare enterprise, as well as one desktop workstation used for all business day activities of any healthcare professional, PACS is considered as a platform for growing into a general IT solution for the majority of IT oriented services of healthcare enterprises.

Medical imaging devices now produce diagnostic images in a digital representation. The digital representation typically includes a two dimensional raster of the image equipped with a header including collateral information with respect to the image itself, patient demographics, imaging technology, and other data used for proper presentation and diagnostic interpretation of the image. Often, diagnostic images are grouped in series, each series representing images that have some commonality and differ in one or more details. For example, images representing anatomical cross-sections of a human body substantially normal to its vertical axis and differing by their position on that axis from top (head) to bottom (feet) are grouped in so-called axial series. A single medical exam, often referred as a "study" or an "exam," typically includes one or more series of images, such as images exposed before and after injection of contrast material or images with different orientation or differing by any other relevant circumstance(s) of imaging procedure. The digital images are forwarded to specialized archives equipped for safe storage, search, access, and distribution of the images and collateral information for successful diagnostic interpretation.

BRIEF SUMMARY

Certain examples provide methods and systems for an application messaging integration framework. An example method includes receiving a user input at a first clinical viewer via an integrated interface. The example method includes sending a message based on the input to a second clinical viewer via an application and messaging integrator. The application and messaging integrator is created to facilitate communication between the first and second clinical viewers. The example method includes updating information at the second clinical viewer based on the message. The example method includes displaying the updated information at the second clinical viewer via the integrated interface.

Another example method includes instantiating an application and messaging integrator to facilitate communication between a first clinical viewer and a second clinical viewer. A single integrated interface is provided to access the first and second clinical viewers and the integrated interface includes options from both a first clinical viewer interface and a second clinical viewer interface integrated into the single integrated interface. The example method includes receiving a user input at the first clinical viewer via the single integrated interface. The example method includes operating on the user input via the first clinical viewer. The example method includes sharing the user input with the second clinical viewer by sending a message based on the user input to the second clinical viewer via the application and messaging integrator.

An example system includes a first clinical viewer to receive a user input via an integrated interface. The example system includes an application and messaging integrator to send a message based on the input. The example system includes a second clinical viewer to receive the message and update information based on the message. The updated information is displayed at the second clinical viewer via the integrated interface.

Another example system includes a first clinical viewer to instantiate an application and messaging integrator to facilitate communication between the first clinical viewer and a second clinical viewer. A single integrated interface is provided to access the first and second clinical viewers and the integrated interface includes options from both a first clinical viewer interface and a second clinical viewer interface integrated into the single integrated interface. The first clinical viewer receives a user input via the single integrated interface and operates on the user input. The first clinical viewer shares the user input with the second clinical viewer by sending a message based on the user input to the second clinical viewer via the application and messaging integrator.

Figure 1:
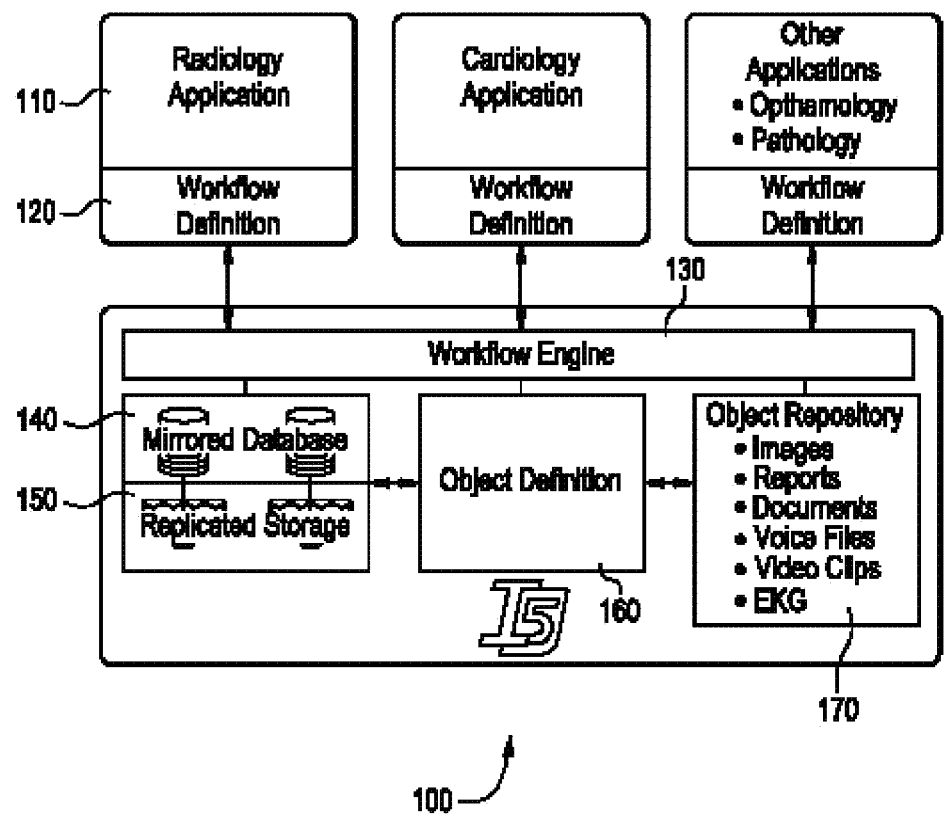
FIG. 1 illustrates an example business and application diagram for a PACS information system in accordance with certain embodiments of the present invention.

The foregoing summary, as well as the following detailed description of certain examples of the present invention, will be better understood when read in conjunction with the appended drawings. For the purpose of illustrating the invention, certain examples are shown in the drawings. It should be understood, however, that the present invention is not limited to the arrangements and instrumentality shown in the attached drawings.

DETAILED DESCRIPTION OF CERTAIN EXAMPLES

Certain examples relate to integration between systems via a common viewer and framework. Certain examples relate to front end integration between an image viewer and image processing client using a common back end messaging framework. Certain examples provide an integration framework for user consistency and true integration between two separate applications, such as an image processing system ("AW") and an Internet and web-accessible PACS ("IW"), to allow them to run together on one workstation via one viewer. Such applications may include, for example, General Electric® Advanced Windows Workstation ("AW client") and General Electric® PACS-IW ("IW viewer") applications. A shared context and a single message loop, combined with re-parenting of the two applications in a single application view, provide tighter integration than two applications merely running on the same machine. Certain examples allow messages and contest to be shared between the applications so that each application is aware of messages for the other application and the current context. Certain examples provide a common user interface ("UI"), same window consistency, same user events, etc., while still having two separate applications in reality.

Conversely, in prior systems, two disparate applications could be housed on the same machine and allowed to share files but were not really integrated. Two sets of messages were needed, one for each application. Traditionally, these were two separate applications running on two separate machines.

Some examples described herein provide a context-sensitive tool bar. For example, a toolbar located at a top of a display is sensitive to a user and/or system configuration (e.g., specific items for a type of study, etc.). In some examples, the tool bar is visible on each viewport (e.g., a placeholder window in a viewing application) so that the content of the viewport drives that toolbar. Thus, the toolbar must be cognizant of the data in the viewport.

Certain examples provide an information system 100 for a healthcare enterprise including a PACS system for radiology and/or other subspecialty system as demonstrated by the business and application diagram in FIG. 1. The system 100 of FIG. 1 includes a clinical application 110, such as a radiology, cardiology, ophthalmology, pathology, and/or other application. The system 100 also includes a workflow definition 120 for each application 110. The workflow definitions 120 communicate with a workflow engine 130. The workflow engine 130 is in communication with a mirrored database 140, object definitions 160, and an object repository 170. The mirrored database 140 is in communication with a replicated storage 150. The object repository 170 includes data such as images, reports, documents, voice files, video clips, EKG information, etc.

Figure 2:
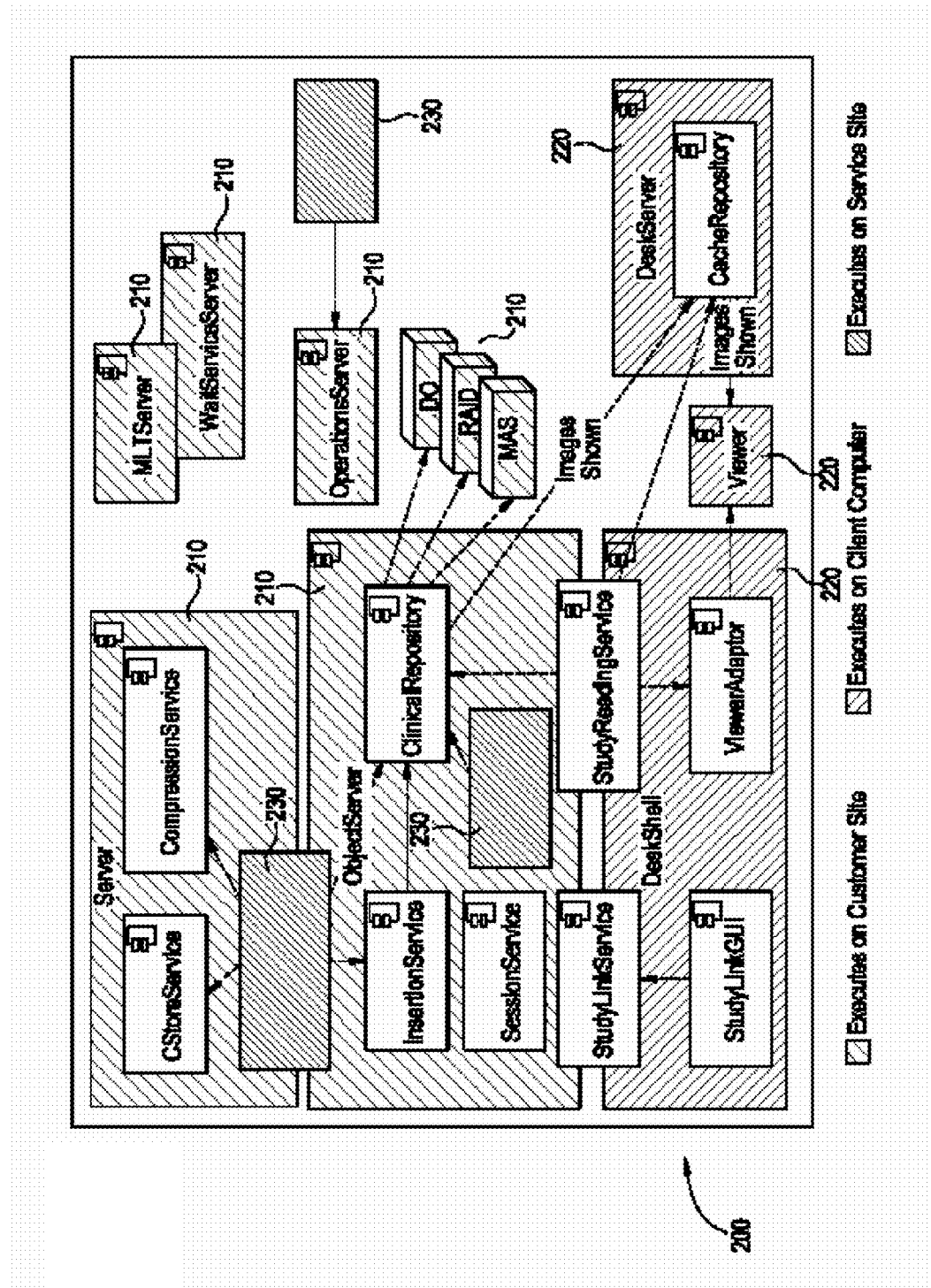
FIG. 2 illustrates an example information system delivering application and business content in accordance with certain embodiments of the present invention.

An example of an information system 200 that delivers application and business goals is presented in FIG. 2. The information system 200 of FIG. 2 demonstrates services divided among a service site 230, a customer site 210, and a client computer 220. For example, a Dicom Server, HL7 Server, Web Services Server, Operations Server, database and other storage, an Object Server, and a Clinical Repository execute on a customer site 210. A Desk Shell, a Viewer, and a Desk Server execute on a client computer 220. A Dicom Controller, Compiler, and the like execute on a service site 230. Thus, operational and data workflow may be divided, and only a small display workload is placed on the client computer 220, for example.

Certain examples provide an architecture and framework for a variety of clinical applications. The framework can include front-end components including but not limited to a Graphical User Interface ("GUI") and can be a thin client and/or thick client system to varying degree, with some or all applications and processing running on a client workstation, on a server, and/or running partially on a client workstation and partially on a server, for example.

Figure 3:
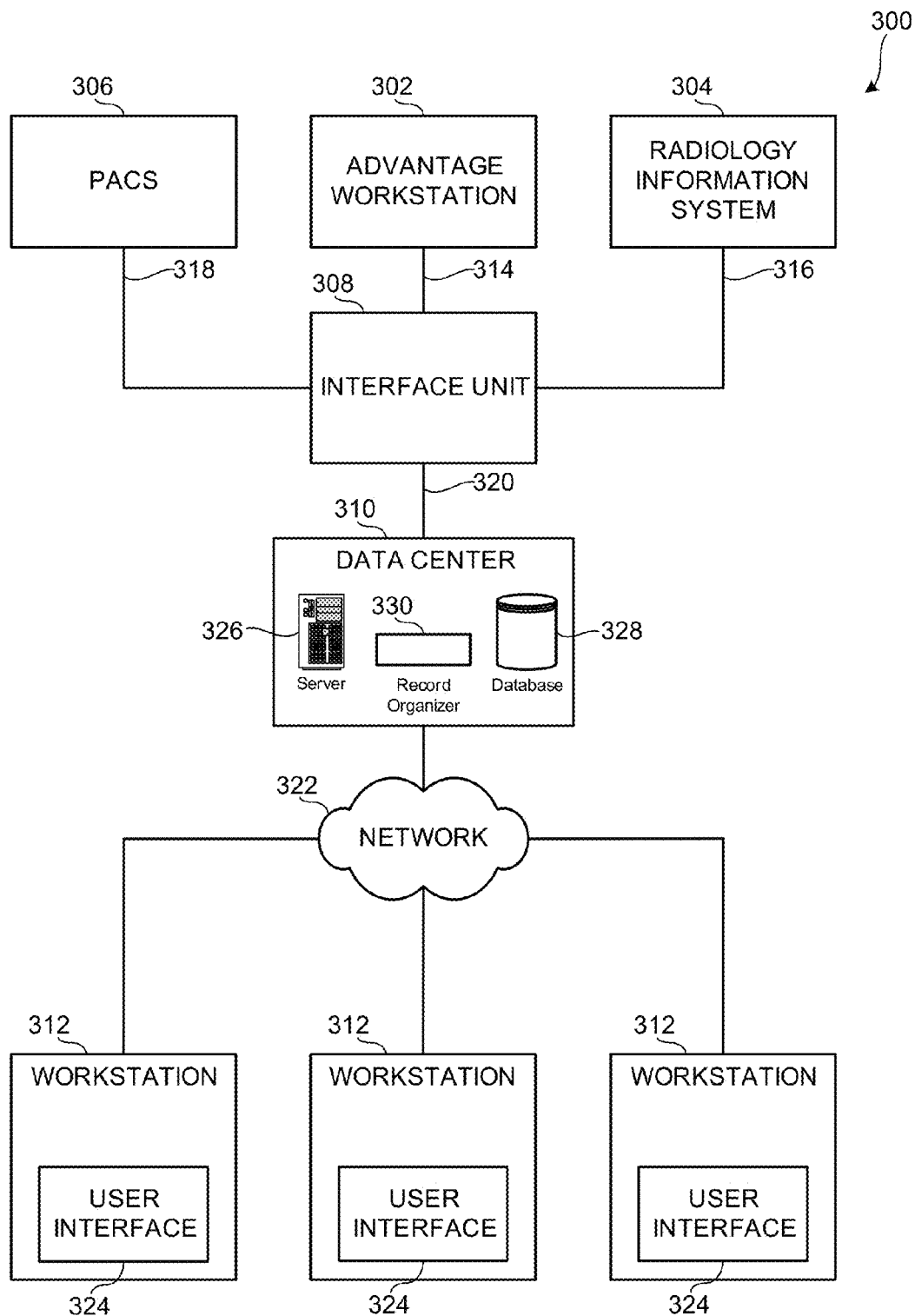
FIG. 3 illustrates a block diagram of an example clinical information system that may be used to implement systems and methods described herein.

FIG. 3 shows a block diagram of an example clinical information system 300 capable of implementing the example methods and systems described herein. The example clinical information system 300 includes a clinical application or advantage workstation ("AW") 302, a radiology information system ("RIS") 304, a picture archiving and communication system ("PACS") 306, an interface unit 308, a data center 310, and a plurality of workstations 312. In the illustrated example, the AW 302, the RIS 304, and the PACS 306 are housed in a healthcare facility and locally archived. However, in other implementations, the AW 302, the RIS 304, and/or the PACS 306 may be housed one or more other suitable locations. In certain implementations, one or more of the PACS 306, RIS 304, AW 302, etc., can be implemented remotely via a thin client and/or downloadable software solution. Furthermore, one or more components of the clinical information system 300 may be combined and/or implemented together. For example, the RIS 304 and/or the PACS 306 may be integrated with the AW 302; the PACS 306 may be integrated with the RIS 304; and/or the three example information systems 302, 304, and/or 306 may be integrated together. In other example implementations, the clinical information system 300 includes a subset of the illustrated information systems 302, 304, and/or 306. For example, the clinical information system 300 may include only one or two of the AW 302, the RIS 304, and/or the PACS 306. Preferably, information (e.g., image data, image analysis, processing, scheduling, test results, observations, diagnosis, etc.) is entered into the AW 302, the RIS 304, and/or the PACS 306 by healthcare practitioners (e.g., radiologists, physicians, and/or technicians) before and/or after patient examination.

The AW 302 provides post-processing and synergized imaging techniques, across CT, MRI, PET, SPECT, Interventional, etc. The AW 302 can provide 2D, 3D, and/or 4D post-processing workstations as well as facilitate remote review and sharing of images in real time. The RIS 304 stores information such as, for example, radiology reports, messages, warnings, alerts, patient scheduling information, patient demographic data, patient tracking information, and/or physician and patient status monitors. Additionally, the RIS 304 enables exam order entry (e.g., ordering an x-ray of a patient) and image and film tracking (e.g., tracking identities of one or more people that have checked out a film). In some examples, information in the RIS 304 is formatted according to the HL-7 (Health Level Seven) clinical communication protocol.

The PACS 306 stores medical images (e.g., x-rays, scans, three-dimensional renderings, etc.) as, for example, digital images in a database or registry. In some examples, the medical images are stored in the PACS 306 using the Digital Imaging and Communications in Medicine ("DICOM") format. Images are stored in the PACS 306 by healthcare practitioners (e.g., imaging technicians, physicians, radiologists) after a medical imaging of a patient and/or are automatically transmitted from medical imaging devices to the PACS 306 for storage. In some examples, the PACS 306 may also include a display device and/or viewing workstation to enable a healthcare practitioner to communicate with the PACS 306.

The interface unit 308 includes a hospital information system interface connection 314, a radiology information system interface connection 316, a PACS interface connection 318, and a data center interface connection 320. The interface unit 308 facilities communication among the AW 302, the RIS 304, the PACS 306, and/or the data center 310. The interface connections 314, 316, 318, and 320 may be implemented by, for example, a Wide Area Network ("WAN") such as a private network or the Internet. Accordingly, the interface unit 308 includes one or more communication components such as, for example, an Ethernet device, an asynchronous transfer mode ("ATM") device, an 802.11 device, a DSL modem, a cable modem, a cellular modem, etc. In turn, the data center 310 communicates with the plurality of workstations 312, via a network 322, implemented at a plurality of locations (e.g., a hospital, clinic, doctor's office, other medical office, or terminal, etc.). The network 322 is implemented by, for example, the Internet, an intranet, a private network, a wired or wireless Local Area Network, and/or a wired or wireless Wide Area Network. In some examples, the interface unit 308 also includes a broker (e.g., a Mitra Imaging's PACS Broker) to allow medical information and medical images to be transmitted together and stored together.

In operation, the interface unit 308 receives images, medical reports, administrative information, and/or other clinical information from the information systems 302, 304, 306 via the interface connections 314, 316, 318. If necessary (e.g., when different formats of the received information are incompatible), the interface unit 308 translates or reformats (e.g., into Structured Query Language ("SQL") or standard text) the medical information, such as medical reports, to be properly stored at the data center 310. Preferably, the reformatted medical information may be transmitted using a transmission protocol to enable different medical information to share common identification elements, such as a patient name or social security number. Next, the interface unit 308 transmits the medical information to the data center 310 via the data center interface connection 320. Finally, medical information is stored in the data center 310 in, for example, the DICOM format, which enables medical images and corresponding medical information to be transmitted and stored together.

The medical information is later viewable and easily retrievable at one or more of the workstations 312 (e.g., by their common identification element, such as a patient name or record number). The workstations 312 may be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. The workstations 312 receive commands and/or other input from a user via, for example, a keyboard, mouse, track ball, microphone, etc. As shown in FIG. 3, the workstations 312 are connected to the network 322 and, thus, can communicate with each other, the data center 310, and/or any other device coupled to the network 322. The workstations 312 are capable of implementing a user interface 324 to enable a healthcare practitioner to interact with the clinical information system 300. For example, in response to a request from a physician, the user interface 324 presents a patient medical history. Additionally, the user interface 324 includes one or more options related to the example methods and apparatus described herein to organize such a medical history using classification and severity parameters.

The example data center 310 of FIG. 3 is an archive to store information such as, for example, images, data, medical reports, and/or, more generally, patient medical records. In addition, the data center 310 may also serve as a central conduit to information located at other sources such as, for example, local archives, hospital information systems/radiology information systems (e.g., the HIS 302 and/or the RIS 304), or medical imaging/storage systems (e.g., the PACS 306 and/or connected imaging modalities). That is, the data center 310 may store links or indicators (e.g., identification numbers, patient names, or record numbers) to information. In the illustrated example, the data center 310 is managed by an application server provider ("ASP") and is located in a centralized location that may be accessed by a plurality of systems and facilities (e.g., hospitals, clinics, doctor's offices, other medical offices, and/or terminals). In some examples, the data center 310 may be spatially distant from the AW 302, the RIS 304, and/or the PACS 306 (e.g., at General Electric® headquarters). In certain examples, the AW 302 can be integrated with one or more of the PACS 306, RIS 304, etc., via a messaging framework and viewer.

The example data center 310 of FIG. 3 includes a server 326, a database 328, and a record organizer 330. The server 326 receives, processes, and conveys information to and from the components of the clinical information system 300. The database 328 stores the medical information described herein and provides access thereto. The example record organizer 330 of FIG. 3 manages patient medical histories, for example. The record organizer 330 can also assist in procedure scheduling, for example.

Figure 4:
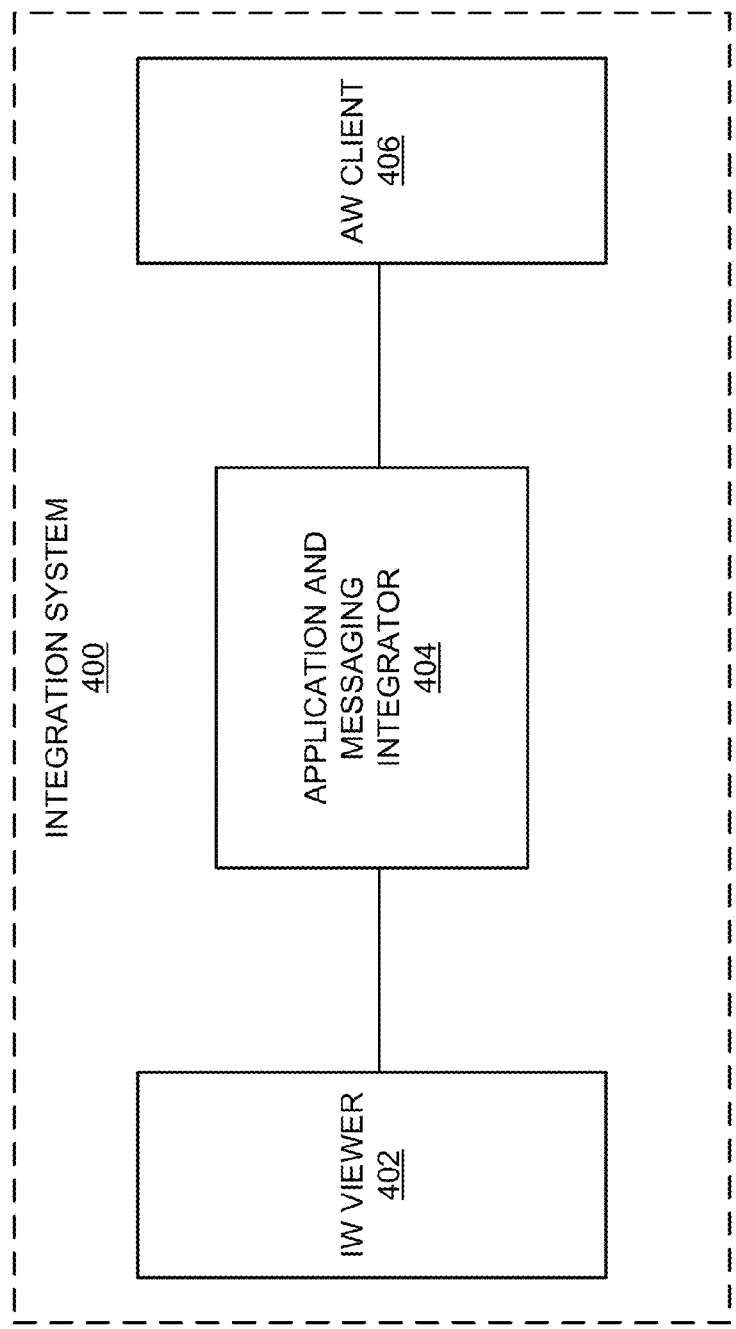
FIG. 4 illustrates a block diagram of an example integration system that may be used to implement systems and methods described herein.

FIG. 4 illustrates a block diagram of an example integration system 400 that may be used to implement systems and methods described herein. FIG. 4 provides the integration system 400 for user consistency and true integration between two separate applications, such as an IW viewer 402 and an AW client 406. The integration system 400 allows the IW viewer 402 and the AW client 406 to run together on one workstation (e.g., the workstation 312 of FIG. 3) via one viewer (e.g., the user interface 324). A shared context and a single message loop, combined with re-parenting of the IW viewer 402 and the AW client 406 in a single application view, provide tighter integration than two applications merely running on the same machine.

Re-parenting allows an application started within a root window (e.g., the whole screen) to be adopted by (e.g., put inside of) another window. Re-parenting allows contents of one window to be added and/or arranged within another window such that the content appears to a user as being a part of the same program. Re-parenting may arrange one or more programs into the same window and may combine tiling and stacking in various ways. Window buttons, window titles, title bars, tool bars, etc., may be created during re-parenting.

Through tight integration (e.g., including re-parenting) between the IW viewer 402 and the AW client 406, the combined functionality appears as a single product to a user, who interacts with both sets of functionality through a single interface. The same user interface, same window consistency, shared user events, etc., can be used to join the IW viewer 402 and the AW client 406 applications and still provide consistency for a user. The integration system 400 allows for messaging between the IW viewer 402 and the AW client 406. Rather than two disparate applications sharing files, the IW viewer 402 and the AW client 406 are re-parented to have a single application view presented to the user. Messaging occurs between the IW viewer 402 and the AW client 406 via an application and messaging integrator 404 to provide a single message loop. For example, messages sent to one application (e.g., the IW viewer 402) are also provided to the other application (e.g., the AW client 406) so that the second application (e.g., the AW client 406) is aware of the messages.

In some examples, a shared context is provided for the IW viewer 402 and the AW client 406, while in the background the IW viewer 402 and the AW client 406 remain two separate applications. In some examples, a language is defined between the IW viewer 402 and the AW client 406 such as each application communicates with and understands the same language for commands, data, etc.

Some examples provide a single user environment (e.g., the user interface 324) managed seamlessly by the user. The user does not know which application (e.g., the IW viewer 402 and the AW client 406) is doing what. In some examples, an abstraction layer provides a single point of user input directed to different subscribers of that user input while ensuring that each application (e.g., the IW viewer 402 and the AW client 406) is abstracted from that single input. Some examples provide front end integration using the application and messaging integrator 404 between the IW viewer 402 and the AW client 406 using sockets.

In the example of FIG. 4, the IW viewer 402 creates an instance of the front-end application and messaging integrator 404. The front-end application and messaging integrator 404 creates an IW server socket with which an AW client socket of the AW client 406 can connect. The AW client 406 creates a sever socket with which an IW client socket of the application and messaging integrator 404 can connect. Server socket(s) can also be used to receive data from the other party, and client socket(s) can also be used to send data to the other party.

In certain examples, a message (e.g., WM_LISTENER_GOT_DATA) is generated and sent from the application and messaging integrator 404 to the IW viewer 402 after data has arrived over the IW server socket. To send data, the IW viewer 402 calls application and messaging integrator data member functions to send data over the IW client socket.

In certain examples, the application and messaging integrator 404 includes a wrapper (e.g., CIW_AW_Wrapper), which is a high level front-end application and messaging integrator to integrate the IW viewer 402 and the AW client 406 together. At a low level, CIW_AW_Wrapper uses socket communication (e.g., IW_AW_SocketComm) to send and read data over sockets. A workflow in which the IW viewer 402 uses CIW_AW_Wrapper to communicate with the AW client 406 is described further below.

Figure 5:
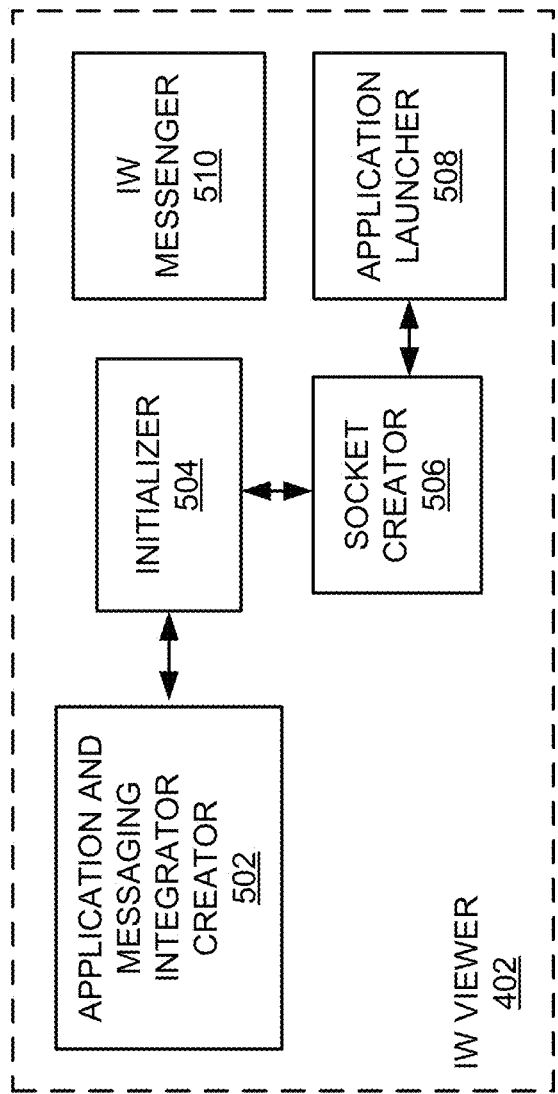
FIG. 5 illustrates a block diagram of an example IW viewer of FIG. 4.

FIG. 5 illustrates a block diagram of an example IW viewer 402 of FIG. 4. The IW viewer 402 of the illustrated example operates as part of the integration system 400 of FIG. 4 to facilitate communication with the AW client 406 to allow both the IW viewer 402 and the AW client 406 to run together on one workstation (e.g., the workstation 312 of FIG. 3) via one viewer (e.g. the user interface 324).

In the example of FIG. 5, the IW viewer 402 creates an instance of the front-end application and messaging integrator 404 of FIG. 4. The front-end application and messaging integrator 404 creates an IW server socket with which an AW client socket of the AW client 406 can connect. The AW client 406 creates a sever socket with which an IW client socket of the application and messaging integrator 404 can connect. A message (e.g., WM_LISTENER_GOT_DATA) is generated and sent from the application and messaging integrator 404 to the IW viewer 402 after data has arrived over the IW server socket. To send data, the IW viewer 402 calls application and messaging integrator data member functions to send data over the IW client socket. In the example of FIG. 5, the application and messaging integrator 404 includes a wrapper (e.g., CIW_AW_Wrapper), which is a high level front-end application and messaging integrator to integrate the IW viewer 402 and the AW client 406 together. At a low level, CIW_

AW_Wrapper uses socket communication (e.g., IW_AW_SocketComm) to send and read data over sockets.

The IW viewer 402 of the illustrated example includes an application and messaging integrator creator 502, an initialize 504, a socket creator 506, an application launcher 508, and an IW messenger 510. The application and messaging integrator creator 502 of the illustrated example creates an instance of the application and messaging integrator 404. The application and messaging integrator creator 502 creates instances of application and messaging integrator to facilitate communication with the AW client 406.

The initializer 504 of the illustrated example is used to initialize the integration system 400 of FIG. 4. The initializer 504 initializes the integration system 400 by defining integration parameters. For example, the initializer 504 calls Initialize( ) with two parameters. The first parameter for Initialize( ) is the IW main window handle. The second parameter for Initialize( ) is a windows message identifier (e.g., WM_LISTENER_GOT_DATA). The initializer 504 calls SetupServer( ) after calling Initialize( ). SetupServer( ) accepts three parameters. The first parameter is for the IW viewer 402 client address and may be, for example, "localhost" for many cases. The second parameter specifies a desired port number. If a desired port number is specified with SetupServer( ), but is not available in the operating system, SetupServer( ) will return a fail result (e.g., an error). If the second parameter is null, SetupServer( ) allows the operating system to choose a port number. If the operating system successfully finds one available port, SetupServer( ) returns a success result with the chosen port number as the third parameter.

The initializer 504 calls SetupClient( ) after calling SetupServer( ) to set up the AW client 406. SetupClient( ) may be called once the AW client 406 has a server socket ready to accept a connecting request. SetupClient( ) has two parameters. The first parameter holds the network address of the AW client 406. The second parameter holds the port number that the AW client 406 will listen to. The IW viewer 402 uses this port to send data to the AW client 406 via the application and messaging integrator 404.

The initializer 504 initializes the AW client 406. For example, the initializer uses a thread InitAW( ) to initialize the AW client 406. The thread InitAW( ) attempts to start an AW application and connect with the AW client 406 in, for example, three seconds. If the AW application is not started successfully (e.g., in three seconds), a time out error is generated. If the AW application is started successfully, the AW client 406 sends a notification to the IW viewer 402 via the application and messaging integrator 404. For example, the AW client 406 sends a "NotifyAWStarted" Extensible Markup Language ("xml") message to the application and messaging integrator 404. The application and messaging integrator 404 generates a WM_LISTENER_GOT_DATA message and sends the message to the IW messenger 510 to notify the IW viewer 402 that data was received from the AW client 406. The IW messenger 510 is used to perform messaging between the IW viewer 402 and other applications (e.g., the AW client 406).

Once the IW viewer 402 has received a notification that an AW application has started successfully (e.g., once a "NotifyAWStarted" message is recognized), the socket creator 506 creates a client socket at the application and messaging integrator 404. For example, the socket creator 506 may use ConnectClient( ) to setup the IW client socket at the application and messaging integrator 404. The IW client socket is used to send messages and/or data to the AW client 406.

The application launcher 508 is used to launch an AW window with a study. For example, an AW window may display a study (e.g., a 2D or 3D study) of chest images acquired from a computed tomography (CT) scanner. To launch an AW window, the application launcher 508 calls SendLoginToAW( ) to inform the AW client 406 of the IW viewer 402 server URL and the AW client 406 server URL. After login succeeds, the application launcher 508 calls SendLaunchApp( ) to send a "LaunchApp" xml message to the AW client 406 with an instance identifier, an application identifier, a study type, and a study identifier to launch an AW window.

The application and messaging integrator 404 created by the application and messaging integrator creator 502 uses the windows message identifier WM_LISTENER_GOT_DATA to notify the IW viewer 402 when data arrives (e.g., from the AW client 406). The IW messenger 510 of the illustrated example creates an event handler to handle the WM_LISTENER_GOT_DATA message received from the application and messaging integrator 404. If a WM_LISTENER_GOT_DATA message with WPARAM as "−1" is received by the IW messenger 510, it means an error has occurred and error handling should be invoked. If a WM_LISTENER_GOT_DATA message with WPARAM as "0" is received by the IW messenger 510, the event handler created by the IW messenger 510 calls GetDataAndMessageType( ) to retrieve data from the application and messaging integrator 404 via a server socket and to recognize the xml message type.

The application and messaging integrator 404 uses ReadingThread( ) to read data from the AW client 406 (e.g., via an IW server socket). If data has been completely read out, ReadingThread( ) notifies the IW messenger 510 with a windows message whose identifier is defined in Initialize( ) (e.g., WM_LISTENER_GOT_DATA) and the IW messenger 510 extracts messages from the message queue. The IW messenger 510 may call GetReceivedData( ) to retrieve data as a byte array from read buffer. Data may be converted from a UTF8 format byte array into a wstring. ReadingThread( ) continues to read data from the IW server socket on the application and messaging integrator 404 until StopListener( ) is called.

If the connection between the IW viewer 402 and the AW client 406 is lost, ReadingThread( ) sends the IW viewer 402 a predefined windows message with WPARAM as "−1" to notify the IW viewer 402 of this error. If an error occurs when sending data, the IW messenger 510 may use GetError( ) to determine what error occurred. If an error occurs when receiving data, the IW messenger may use GetServerSocketError( ) to determine what error occurred.

If the AW client 406 launches an application with a study properly (e.g., without errors), the AW client 406 sends a "NotifyWindowCreated" xml message to the IW messenger 510. After the "NotifyWindowCreated" message is received, the IW viewer 402 creates a child window to display the study (e.g., a 3D study).

The IW messenger 510 may use SendMessage( ) to send an xml message to the AW client 406. The message is converted from a wstring into a UTF8 byte array, for example. SendMessageWithConfirmation( ) may also be used to send message to the AW client 406. SendMessageWithConfirmation( ) also reads the response from the AW client 406 in the IW client socket at the application and messaging integrator 404.

When the IW viewer 402 closes, the socket creator 506 calls CloseServerSocket( ) to close the server socket that was created at the application and messaging integrator 404. The IW messenger 510 calls CloseRemoteClient( ) to send a "Terminate" xml message to the AW client 406 so that the AW client 406 may terminate its application.

As described above, the IW viewer 402 of the illustrated example operates as part of the integration system 400 of FIG. 4 to facilitate communication with the AW client 406 to allow both the IW viewer 402 and the AW client 406 to run together on one workstation via one viewer. The application and messaging integrator 404 provides an abstraction layer and facilitates message-passing for integrated execution of and interaction with the combined IW viewer 402 and AW client 406 by a user.

While the example IW viewer 402 has been illustrated in FIG. 5, one or more of the elements, processes and/or devices illustrated in FIG. 5 may be combined, divided, re-arranged, omitted, eliminated and/or implemented in any other way. Further, the application and messaging integrator creator 502, the initializer 504, the socket creator 506, the application launcher 508, the IW messenger 510, and/or, more generally, the example IW viewer 402 of FIG. 5 may be implemented by hardware, software, firmware and/or any combination of hardware, software and/or firmware. Thus, for example, any of the example application and messaging integrator creator 502, the initializer 504, the socket creator 506, the application launcher 508, the IW messenger 510, and/or, more generally, the example IW viewer 402 of FIG. 5 could be implemented by one or more circuit(s), programmable processor(s), application specific integrated circuit(s) ("ASIC(s)"), programmable logic device(s) ("PLD(s)") and/or field programmable logic device(s) ("FPLD(s)"), etc. When any of the apparatus or system claims of this patent are read to cover a purely software and/or firmware implementation, at least one of the example application and messaging integrator creator 502, the initializer 504, the socket creator 506, the application launcher 508, and/or the IW messenger 510 are hereby expressly defined to include a tangible computer readable medium, such as a memory, Blu-ray, digital versatile disk ("DVD"), compact disc ("CD"), etc., storing the software and/or firmware. Further still, the example IW viewer 402 of FIG. 5 may include one or more elements, processes and/or devices in addition to, or instead of, those illustrated in FIG. 5, and/or may include more than one of any or all of the illustrated elements, processes and devices.

Figure 6:
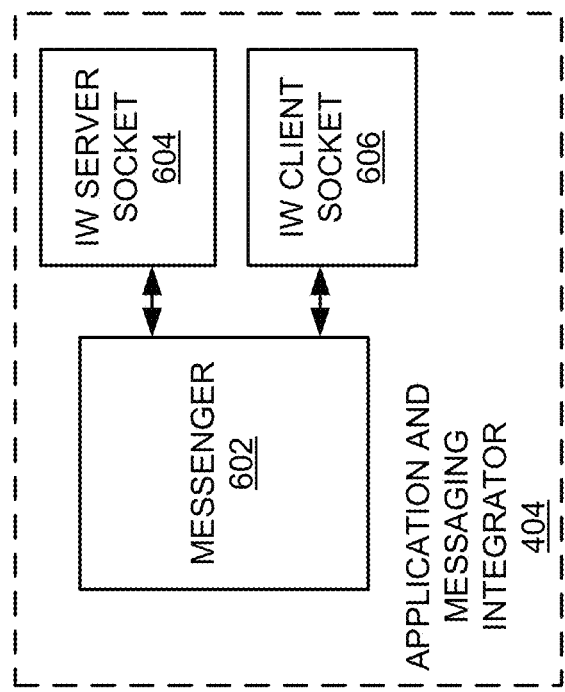
FIG. 6 illustrates a block diagram of an example application and messaging integrator of FIG. 4.

FIG. 6 illustrates a block diagram of an example application and messaging integrator 404 of FIG. 4. The application and messaging integrator 404 of the illustrated example operates as part of the integration system 400 of FIG. 4 to facilitate communication between the IW viewer 402 and the AW client 406 to allow both the IW viewer 402 and the AW client 406 to run together on one workstation (e.g., the workstation 312 of FIG. 3) via one viewer (e.g. the user interface 324). The integration system 400, facilitated by the application and messaging integrator 404, allows the IW viewer 402 and the AW client 406 to operate together and appear as a single product to a user, who interacts with both sets of functionality through a single interface.

In certain examples, the application and messaging integrator 404 is created or spawned by the IW viewer 402 to initiate the integration system 400 of FIG. 4. The application and messaging integrator 404 of the illustrated example includes a messenger 602, an IW server socket 604, and an IW client socket 606.

The messenger 602 of the illustrated example is used to communicate with the IW viewer 402. Once the application and messaging integrator 404 has been created by the IW viewer 402, the messenger 602 creates the IW server socket 604 to facilitate communication with the AW client 406 (e.g., a client socket of the AW client 406). If an AW client 406 application is started successfully, the AW client 406 sends a "NotifyAWStarted" xml message to the application and messaging integrator 404 via the IW server socket 604. The IW server socket 604 sends the notification message to the IW viewer 402 via the messenger 602. Once the notification message is received by the IW viewer 402, the IW viewer 402 instructs the application and messaging integrator 404 via the messenger 602 to create and/or setup the IW client socket 606. The IW client socket 606 is used to send data to applications (e.g., the AW client 406). If the IW viewer 402 wants to send data to the AW client 406, the messenger 602 receives the data from the IW viewer 402 and sends it to the AW client 406 using the IW client socket 606.

When the IW server socket 604 receives data from the AW client 406, the messenger 602 generates and/or sends a windows message (e.g., WM_LISTENER_GOT_DATA) to the IW viewer 402 to notify the IW viewer 402 that data has been received. The IW viewer 402 calls GetDataAndMessageType( ) via the messenger 602 to retrieve data from the IW server socket 604.

The messenger 602 uses ReadingThread( ) to read data from the AW client 406 via the IW server socket 604. If data has been completely read out, ReadingThread( ) notifies the IW viewer 402 with a windows message whose identifier is defined in Initialize( ) (e.g., WM_LISTENER_GOT_DATA) and the IW viewer 402 extracts messages from the message queue. The IW viewer 402 may call GetReceivedData( ) to retrieve data as a byte array from read buffer. Data may be converted from a UTF8 format byte array into a wstring. ReadingThread( ) continues to read data from the IW server socket 604 until StopListener( ) is called.

To launch an AW client 406 window (e.g., study), the IW viewer 402 calls SendLoginToAW( ) via the messenger 602 and IW client socket 606 to inform the AW client 406 of the IW viewer 402 server URL and the AW client 406 server URL. After this login has been successful (e.g., without error), the IW viewer 402 calls SendLaunchApp( ) to send a "LaunchApp" xml message to the AW client 406 via the messenger 602 and the IW client socket 606. The "LaunchApp" message contains, for example, an instance identifier, application identifier, study type, study identifier, etc. to launch an AW client 406 window. If the AW client 406 launches a window appropriately (e.g., without error), the AW client 406 sends a "NotifyWindowCreated" xml message to the IW viewer 402 via the IW server socket 604 and the messenger 602. The IW viewer 402 receives this notification message and creates a window to display the study.

When the IW viewer 402 closes, the IW viewer calls CloseServerSocket( ) via the messenger 602 to close the IW server socket 604. The IW viewer 402 calls CloseRemoteClient( ) to send a "Terminate" xml message to the AW client 406 via the messenger 602 and the IW client socket 606 to instruct the AW client 406 to terminate its application.

The application and messaging integrator 404 facilitates communication between the IW viewer 402 and the AW client 406 to allow both the IW viewer 402 and the AW client 406 to run together on one workstation via one viewer. From a user perspective, the IW viewer 402 and the AW client 406 appear as a single application on an integrated user interface. The IW viewer 402 and the AW client 406 benefit from message-passing and tighter integration provided by the application and message integrator 404.

While the example application and messaging integrator 404 has been illustrated in FIG. 6, one or more of the elements, processes and/or devices illustrated in FIG. 6 may be combined, divided, re-arranged, omitted, eliminated and/or implemented in any other way. Further, the messenger 602, the IW server socket 604, the IW client socket 606, and/or, more generally, the example application and messaging integrator 404 of FIG. 6 may be implemented by hardware, software, firmware and/or any combination of hardware, software and/or firmware. Thus, for example, any of the example messenger 602, the IW server socket 604, the IW client socket 606, and/or, more generally, the example application and messaging integrator 404 of FIG. 6 could be implemented by one or more circuit(s), programmable processor(s), application specific integrated circuit(s) ("ASIC(s)"), programmable logic device(s) ("PLD(s)") and/or field programmable logic device(s) ("FPLD(s)"), etc. When any of the apparatus or system claims of this patent are read to cover a purely software and/or firmware implementation, at least one of the example messenger 602, the IW server socket 604, and/or the IW client socket 606 are hereby expressly defined to include a tangible computer readable medium such as a memory, Blu-Ray, DVD, compact disc ("CD"), etc. storing the software and/or firmware. Further still, the example application and messaging integrator 404 of FIG. 6 may include one or more elements, processes and/or devices in addition to, or instead of, those illustrated in FIG. 6, and/or may include more than one of any or all of the illustrated elements, processes and devices.

Figure 7:
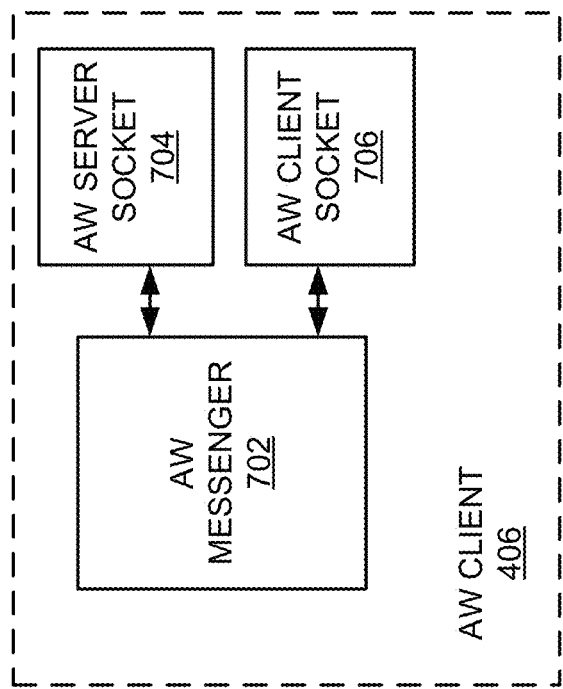
FIG. 7 illustrates a block diagram of an example AW client of FIG. 4.

FIG. 7 illustrates a block diagram of an example AW client 406 of FIG. 4. The AW client 406 of the illustrated example operates as part of the integration system 400 of FIG. 4 to facilitate communication with the IW viewer 402 to allow both the IW viewer 402 and the AW client 406 to run together on one workstation (e.g., the workstation 312 of FIG. 3) via one viewer (e.g. the user interface 324). The AW client 406 of the illustrated example includes an AW messenger 702, an AW server socket 704, and an AW client socket 706.

The AW messenger 702 is used to perform messaging with the AW client 406 and other applications (e.g., the IW viewer 402). The AW messenger 702 uses the AW server socket 704 to receive messages and/or data from, for example, the IW client socket 606 of the application and messaging integrator 404. The AW messenger 702 uses the AW client socket 706 to send messages and/or data to, for example, the IW socket server 604 of the application and messaging integrator 404.

To initialize integration, for example, the IW viewer 402 uses an InitAW( ) thread to initialize the AW client 406. The AW client 406 receives the InitAW( ) thread via the AW server socket 704 and the AW messenger 702. If the AW client 406 application is started successfully (e.g., without error). The AW messenger 702 sends a "NotifyAWStarted" xml message to the application and messaging integrator 404 via the AW client socket 706, for example.

To launch an AW client 406 window (e.g., study), the IW viewer 402 calls SendLoginToAW( ) using the AW server socket 704 and the AW messenger 702 to inform the AW client 406 of the IW viewer 402 server URL and the AW client 406 server URL. After login is successful (e.g., without error), the IW viewer 402 calls SendLaunchApp( ) using the AW server socket 704 and the AW messenger 702 to send a "LaunchApp" xml message to the AW client 406, for example. The launch message includes, for example, an instance identifier, an application identifier, a study type, a study identifier, etc. to launch an AW client 406 window.

When the AW client 406 launches an application, the AW messenger 702 sends a "NotifyWindowCreated" xml message to the application and messaging integrator 404 via the AW client socket 706, for example. The application and messaging integrator 404 sends this notification to the IW viewer 402 to be used to create a window at the IW viewer 402.

When the IW viewer 402 closes, the IW viewer 402 calls CloseRemoteClient( ) to send a "Terminate" xml message to the AW messenger 702 via the AW server socket 704 so that the AW client 406 may terminate its application, for example.

The AW client 406 of the illustrated example operates as part of the integration system 400 of FIG. 4 to facilitate communication with the IW viewer 402 to allow both the IW viewer 402 and the AW client 406 to run together on one workstation via one viewer.

While the example AW client 406 has been illustrated in FIG. 7, one or more of the elements, processes and/or devices illustrated in FIG. 7 may be combined, divided, re-arranged, omitted, eliminated and/or implemented in any other way. Further, the AW messenger 702, the AW server socket 704, the AW client socket 706, and/or, more generally, the example AW client 406 of FIG. 7 may be implemented by hardware, software, firmware and/or any combination of hardware, software and/or firmware. Thus, for example, any of the example AW messenger 702, the AW server socket 704, the AW client socket 706, and/or, more generally, the example AW client 406 of FIG. 7 could be implemented by one or more circuit(s), programmable processor(s), application specific integrated circuit(s) ("ASIC(s)"), programmable logic device(s) ("PLD(s)") and/or field programmable logic device(s) ("FPLD(s)"), etc. When any of the apparatus or system claims of this patent are read to cover a purely software and/or firmware implementation, at least one of the example AW messenger 702, the AW server socket 704, and/or the AW client socket 706 are hereby expressly defined to include a tangible computer readable medium such as a memory, Blu-ray, DVD, compact disc ("CD"), etc. storing the software and/or firmware. Further still, the example AW client 406 of FIG. 7 may include one or more elements, processes and/or devices in addition to, or instead of, those illustrated in FIG. 7, and/or may include more than one of any or all of the illustrated elements, processes and devices.

Flowcharts representative of example machine readable instructions for implementing the example system 400 of FIG. 4 are shown in FIGS. 8-12. In these examples, the machine readable instructions comprise a program for execution by a processor such as the processor 1512 shown in the example processor platform 1500 discussed below in connection with FIG. 15. The program may be embodied in software stored on a tangible computer readable medium such as a compact disc read-only memory ("CD-ROM"), a floppy disk, a hard drive, a digital video disc (DVD), Blu-ray disk, or a memory associated with the processor 1512, but the entire program and/or parts thereof could alternatively be executed by a device other than the processor 1512 and/or embodied in firmware or dedicated hardware. Further, although the example program is described with reference to the flowcharts illustrated in FIGS. 8-12, many other methods of implementing the example system 400 may alternatively be used. For example, the order of execution of the blocks may be changed, and/or some of the blocks described may be changed, eliminated, or combined.

As mentioned above, the example processes of FIGS. 8-12 may be implemented using coded instructions (e.g., computer readable instructions) stored on a tangible computer readable medium such as a hard disk drive, a flash memory, a read-only memory ("ROM"), a CD, a DVD, a Blu-Ray, a cache, a random-access memory ("RAM") and/or any other storage media in which information is stored for any duration (e.g., for extended time periods, permanently, brief instances, for temporarily buffering, and/or for caching of the information). As used herein, the term tangible computer readable medium is expressly defined to include any type of computer readable storage and to exclude propagating signals. Additionally or alternatively, the example processes of FIGS. 8-12 may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals. As used herein, when the phrase "at least" is used as the transition term in a preamble of a claim, it is open-ended in the same manner as the term "comprising" is open ended. Thus, a claim using "at least" as the transition term in its preamble may include elements in addition to those expressly recited in the claim.

Figure 8:
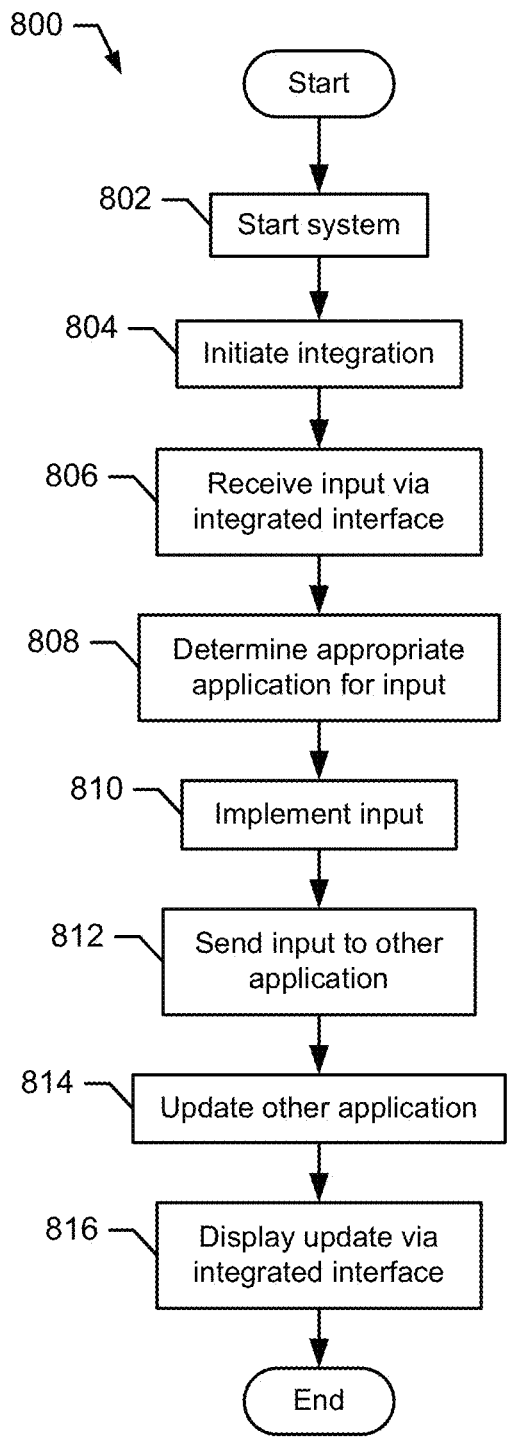
FIG. 8 illustrates a flow diagram of an example method of using the integration system of FIG. 4.

FIG. 8 illustrates a flow diagram of an example method 800 of using the integration system 400 of FIG. 4. The integration system 400 provides front end integration between the IW viewer 402 and AW client 406 using a common back end messaging framework. As shown in FIG. 8, the IW viewer 402 and the AW client 406 run together on one workstation via one viewer. A shared context and a single message loop, combined with re-parenting of the two applications in a single application view, provide tighter integration than two applications merely running on the same machine. As shown in FIG. 8, messages are shared between the applications so that each application is aware of messages for the other application, and each application is also aware of and benefits from the current context (e.g., user and/or patient context).

Initially, the system 400 is started (block 802). The system 400 may be started by, for example, a user powering on a computer, logging into a user account, logging into or otherwise accessing an application, etc. Once the system has been started, integration between the IW viewer 402 and the AW client 406 is initiated (block 804). For example, an abstraction layer may be provided to re-parent the viewer applications 402, 406 and to share messages and data between the IW viewer 402 and the AW client 406. Integration between the IW viewer 402 and the AW client 406 allows the user to use both applications via one unified or integrated interface such that user views the IW viewer 402 and the AW client 406 as one integrated application. Integration of the IW viewer 402 and the AW client 406 is described in greater detail below in connection with FIGS. 9-12.

Once the IW viewer 402 and the AW client 406 have been integrated, the system 400 may receive input from a user via the integrated interface (block 806). The system 400 determines the appropriate application (e.g., the IW viewer 402 or the AW client 406) for the information and/or data input by the user (block 808). For example, the user may input an updated patient record at block 806. The system 400 determines that this information is to be entered into the IW viewer 402, for example, at block 808. The system 400 implements the user input (block 810) by updating the patient record at the IW viewer 402 based on the data entered by the user, for example. The system 400 then sends the input from the appropriate application (e.g., the IW viewer 402) to the other application (e.g., the AW client 406) (block 812). For example, the IW viewer 402 may send the data entered by the user to the AW client 406 via the application and messaging integrator 404. The other application updates its information based on the input of the user (block 814). For example, any information the AW client 406 contains regarding the patient record is updated. The system 400 displays the updated information via the integrated interface (block 816). The updated information may be displayed using the IW viewer 402 or the AW client 406 using the one integrated interface. For example, the user may select a 3D study to be displayed via the one integrated interface and the AW client 406 will provide the study with the updated patient record based on the input of the user that was entered in the IW viewer 402. The method 800 of FIG. 8 allows messages to be shared between the applications so that each application is aware of messages for the other application and the context for each application is updated for use by the user via one integrated interface.

Figure 9:
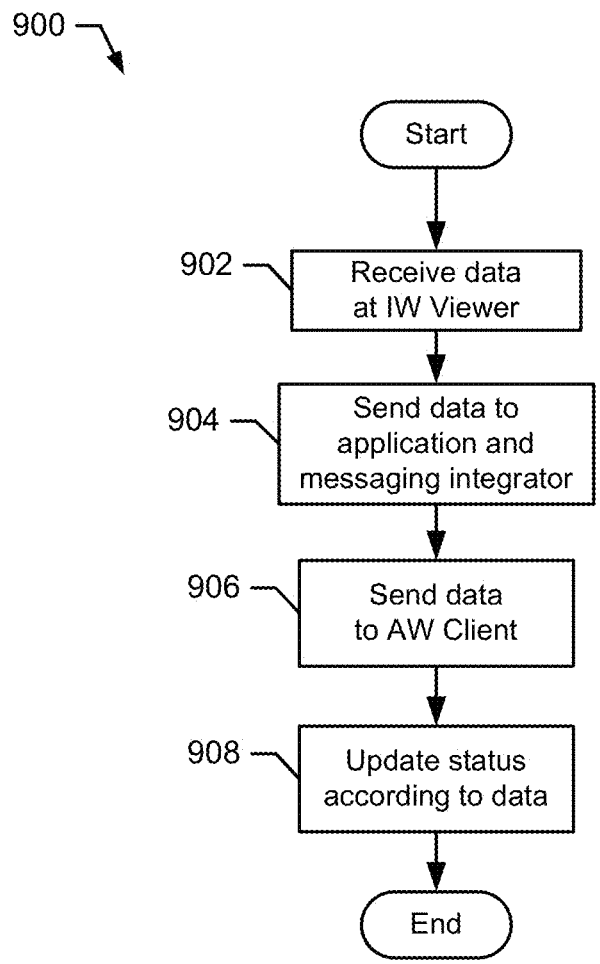
FIG. 9 illustrates a flow diagram of another example method of using the integration system of FIG. 4.

FIG. 9 illustrates a flow diagram of another example method 900 of using the integration system 400 of FIG. 4. The integration system 400 facilitates communication between the IW viewer 402 and the AW client 406 to allow both the IW viewer 402 and the AW client 406 to run together on one workstation (e.g., the workstation 312 of FIG. 3) via one viewer (e.g. the user interface 324).

Initially, data is received at the IW viewer 402 (block 902). Data may be received from, for example, a user and/or an application in a healthcare system. The IW viewer 402 sends the received data to the application and messaging integrator 404 (block 904). The application and messaging integrator sends the received data to the AW client 406 (block 906). The AW client updates according to the data received from the IW viewer 402 via the application and messaging integrator 404 (block 908). The AW client may update, for example, a status, patient information, test results, a diagnosis, etc. based on the received data.

The method 900 of the illustrated example provides for integration between the IW viewer 402 and the AW client 406 so that it appears to a user that he is using only one application, rather than the separate IW viewer 402 and AW client 406. For example, a user may update a patient status on the IW viewer 402 and the method 900 allows the AW client 406 to update any relevant information according to this update entered on the IW viewer 402.

Figure 10:
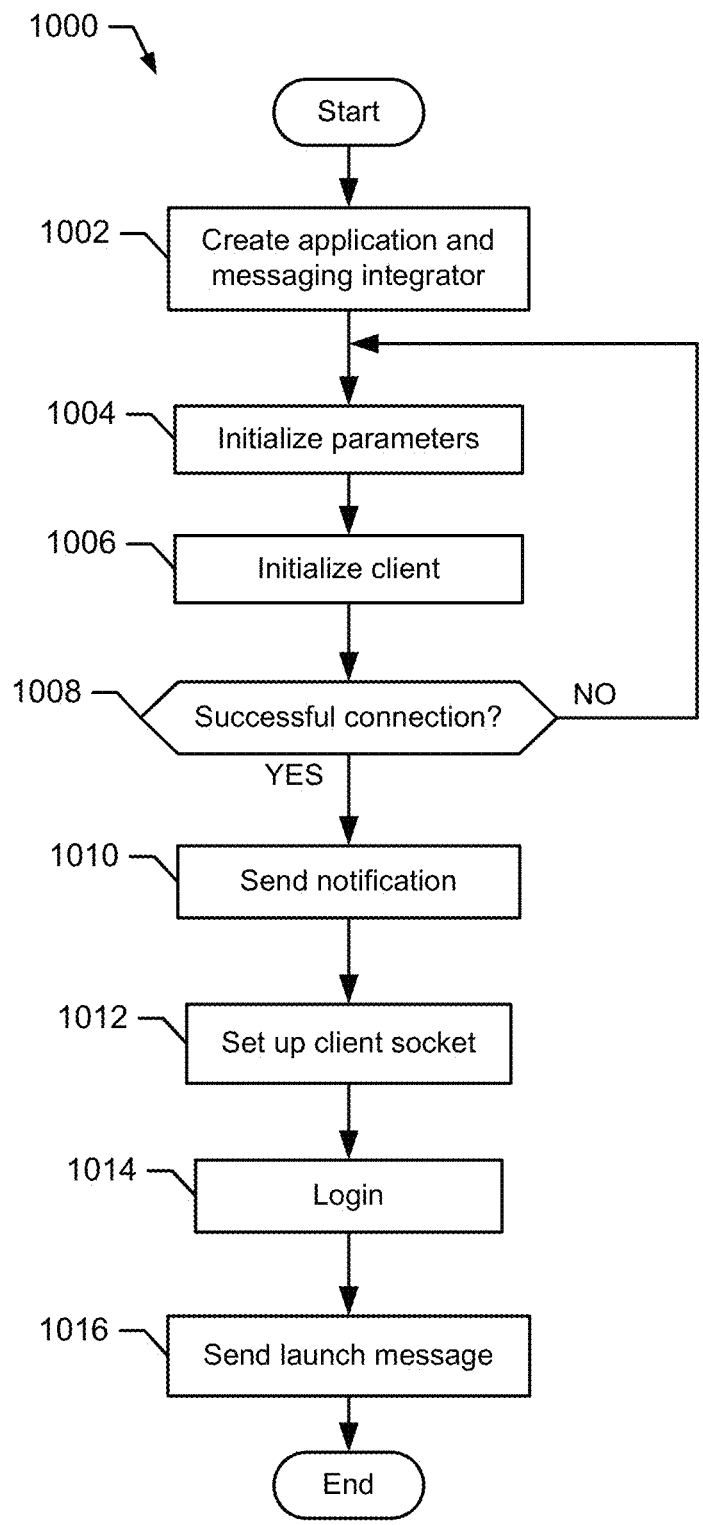
FIG. 10 illustrates a flow diagram of an example method of initializing the integration system of FIG. 4.

FIG. 10 illustrates a flow diagram of an example method 1000 of initializing the integration system 400 of FIG. 4. Initially, the application and messaging integrator creator 502 of the IW viewer 402 of FIG. 5 creates an instance of an application and messaging integrator (e.g., the application and messaging integrator 404) (block 1002). The initializer 502 then initializes parameters (block 1004) by calling Initialize( ) with two parameters. The first parameter for Initialize( ) is an IW viewer 402 main window handle. The second parameter for Initialize( ) is a windows message identifier (e.g., WM_LISTENER_GOT_DATA) that the application and messaging integrator 404 may use to notify the IW viewer 402 when data arrives. The initializer 504 calls SetupServer( ) with three parameters. The first parameter is for the IW viewer 402 client address and may be, for example, "localhost." The second parameter specifies a desired port number. If a desired port number is specified with SetupServer( ), but is not available in the operating system, SetupServer( ) will return an error. If the second parameter is null, SetupServer( ) allows the operating system to choose a port number. If the operating system successfully finds one available port, SetupServer( ) returns a success result with the chosen port number as the third parameter.

The initializer 504 then initializes the AW client 406 (block 1006). The initializer 504 calls SetupClient( ) once the AW client 406 has a server socket ready to accept a connecting request. SetupClient( ) has two parameters. The first parameter holds the network address of the AW client 406. The second parameter holds the port number that the AW client 406 will listen to. The IW viewer 402 uses this port to send data to the AW client 406 via the application and messaging integrator 404. The initializer 504 uses a thread InitAW( ) to initialize the AW client 406. InitAW( ) attempts to start an AW client 406 application and connect with the AW client 406 within a certain period of time (e.g., three seconds) (block 1008). If the AW client 406 is not connected within this period of time, a time out error is generated and control returns to block 1004. If the AW client 406 is connected and the application is started successfully (e.g., without error), the AW client 406 sends a notification message (block 1010) via the AW messenger 702 and the AW client socket 706 of FIG. 7. The notification message is sent to the IW client 402 via the application and messaging integrator 404. The notification message may be, for example, a "NotifyAWStarted" xml message. Once the IW messenger 510 recognizes the "NotifyAWStarted" xml message, the socket creator 506 uses ConnectClient( ) to create an IW client socket 606 at the application and messaging integrator 404 (block 1012).

To launch an AW client 406 window (e.g., study), the AW client 406 is logged in to the IW viewer (block 1014). To login, the application launcher 508 of the IW viewer 402 calls SendLoginToAW( ) to inform the AW client 406 of the IW viewer 402 server URL and the AW client 406 server URL. Once the login is successful, the IW messenger 510 calls SendLaunchApp( ) to send a "LaunchApp" xml message to the AW client 406 (block 1016). The launch message includes, for example, an instance identifier, an application identifier, a study type, a study identifier, etc. to launch the AW client 406 window. Launching an AW client window 406 is described in greater detail below in connection with FIG. 11.

Figure 11:
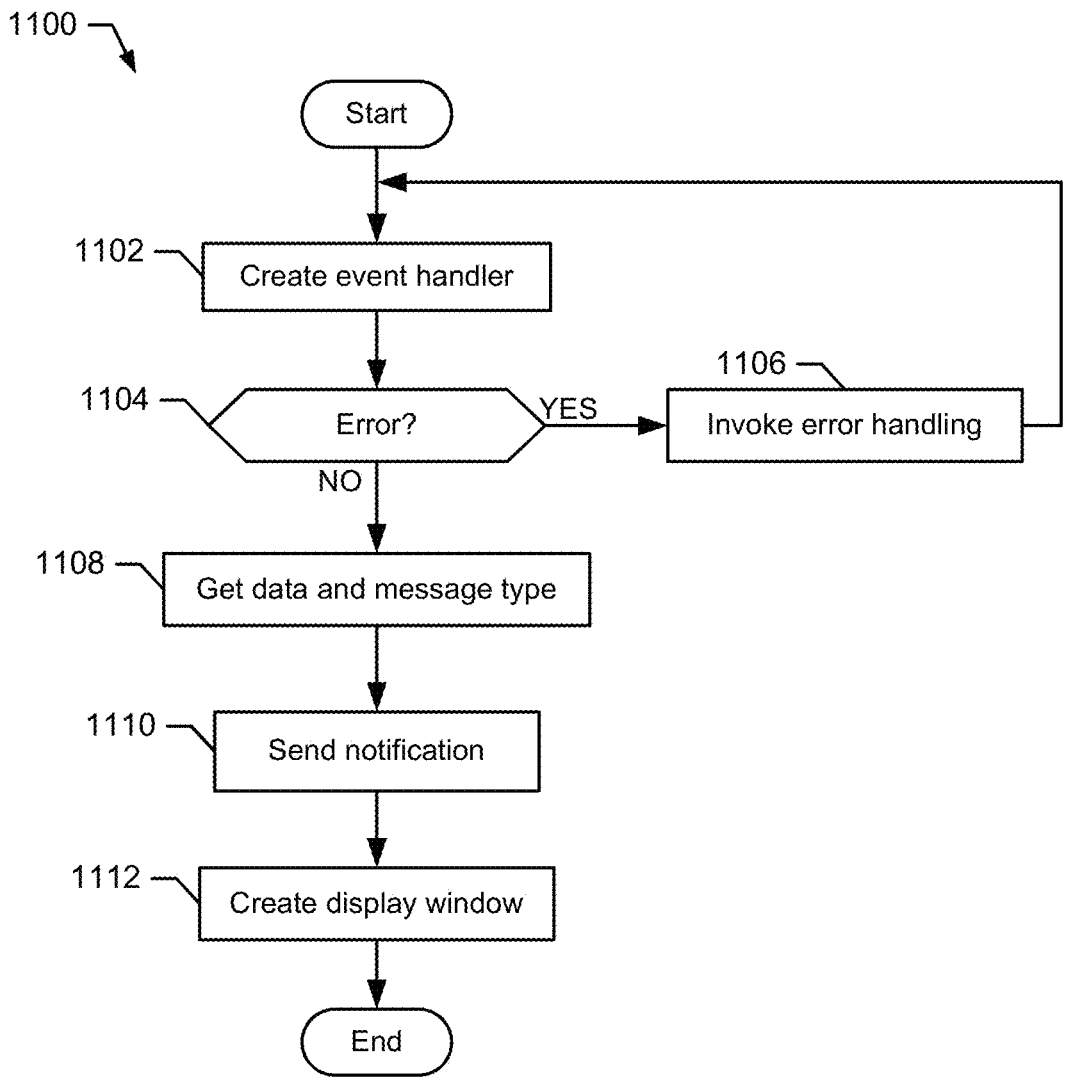
FIG. 11 illustrates a flow diagram of an example method of creating an AW display window using the integration system of FIG. 4.

FIG. 11 illustrates a flow diagram of an example method 1100 of creating an AW client 406 display window using the integration system 400 of FIG. 4. Initially, the IW messenger 510 of the IW viewer 402 creates an event handler (block 1102). The event handler is created to handle the WM_LISTENER_GOT_DATA message that is received by the IW messenger 510 from the messenger 602 of the application and messaging integrator 404 when the application and messaging integrator 404 receives data from the AW client 406. The IW messenger 510 determines if an error has occurred during the sending of the data (block 1104). For example, if a WM_LISTENER_GOT_DATA message with WPARAM as "−1" is received by the IW messenger 510, the IW messenger 510 determines an error has occurred and invokes error handling (block 1106). Control then returns to block 1102 when error handling is completed. If a WM_LISTENER_GOT_DATA message with WPARAM as "0" is received by the IW messenger 510, the IW messenger 510 determines that no error has occurred. The IW viewer then gets data and a message type (block 1108). The event handler created by the IW messenger 510 then calls GetDataAndMessageType( ) to retrieve data from the application and messaging integrator 404 and to recognize the xml message type. The application and messaging integrator 404 uses ReadingThread( ) to read data from the AW client 406 via the IW server socket 604. If data has been completely read out, ReadingThread( ) notifies the IW messenger 510 with WM_LISTENER_GOT_DATA and the IW messenger 510 extracts messages from the message queue. The IW messenger 510 may call GetReceivedData( ) to retrieve data as a byte array from read buffer. Data may be converted from UTF8 format byte array into a w-string. ReadingThread( ) continues to read data from the IW server socket on the application and messaging integrator 404 until StopListener( ) is called.

Once the AW client 406 launches the window, the AW messenger 702 of the AW client 406 sends a "NotifyWindowCreated" xml message to the IW client 402 via the application and messaging integrator 404 (block 1110). Once the IW messenger 510 of the IW client 402 receives the "NotifyWindowCreated" message, the application launcher 508 creates a window (e.g., a child window) in the IW viewer 402 to display the study (block 1112).

Figure 12:
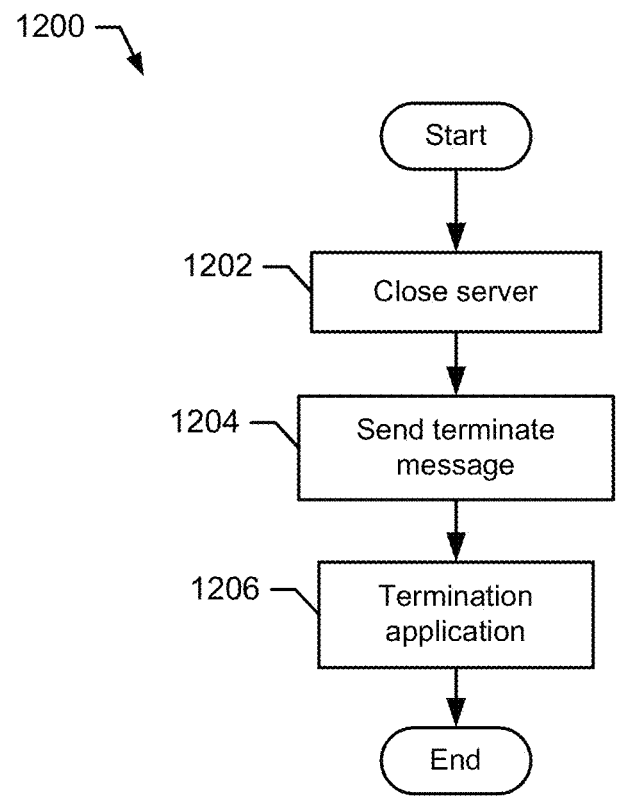
FIG. 12 illustrates a flow diagram of an example method of terminating an application using the integration system of FIG. 4.

FIG. 12 illustrates a flow diagram of an example method 1200 of terminating an application using the integration system 400 of FIG. 4. When the IW viewer 402 closes, the IW messenger 510 calls Close ServerSocket( ) to close the server socket 604 of the application and messaging integrator 404 (block 1202). The IW messenger 510 call CloseRemoteclient( ) to send a "terminate" xml message to the AW client 406 via the application and messaging integrator 404 (block 1204). The AW client 406 terminates the application (block 1206) when it receives the termination message from the IW viewer 402.

Figure 13:
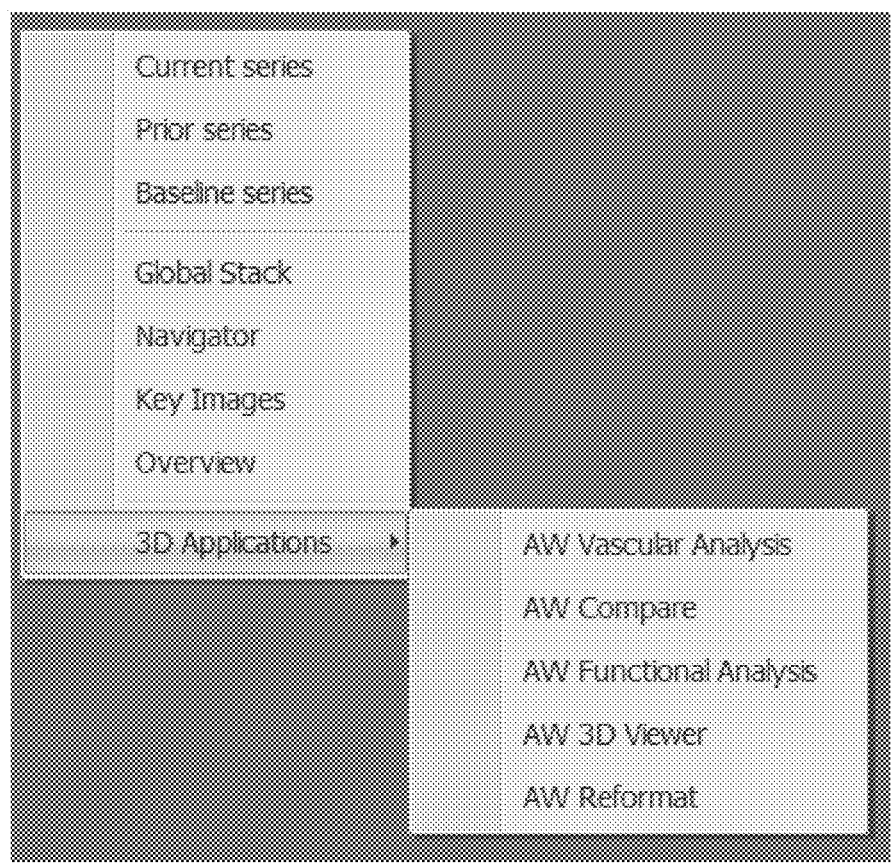
FIG. 13 illustrates an example specialized placeholder added for three-dimensional (3D) applications from AW running with IW in the integrated framework.

FIG. 13 illustrates an example specialized placeholder 1300 added for three-dimensional (3D) applications from AW running with IW in the integrated framework. The placeholder 1200 of the illustrated example provides a context-sensitive tool bar. For example, a toolbar may be located at a top of a display and may be sensitive to a user and/or system configuration (e.g., specific items for a type of study, etc.). In some examples, the tool bar is visible on each viewport (e.g., a placeholder window in a viewing application) so that the content of the viewport drives that toolbar. Thus, the toolbar must be cognizant of the data in the viewport.

In the example of FIG. 13, the new placeholder 1300 can be defined by double-clicking on any empty placeholder in a Hanging Protocol Editor, and then choosing a desired AW 3D application from the pop-up menu, as shown in FIG. 13. Thus, AW client 406 application options and operations can be combined with IW viewer 402 options and operations in an integrated tool bar or set of menu options for user selection.

Figure 14:
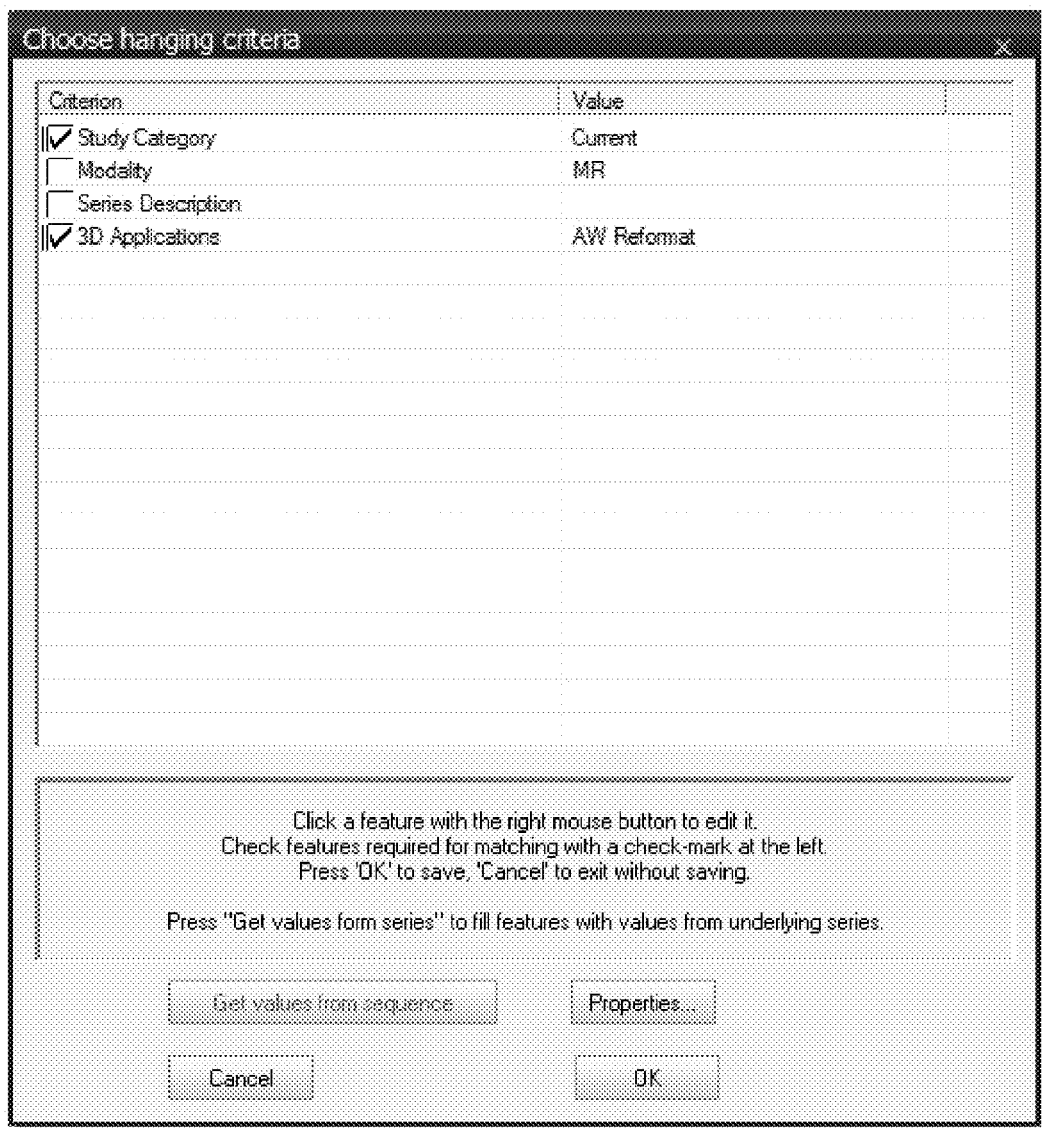
FIG. 14 illustrates an example dialog associated with the placeholder of FIG. 13.

By double-clicking on the defined AW 3D placeholder, or right-clicking on it and then choosing "Hanging features", a "Choose hanging criteria" dialog 1400 can be displayed as shown in the example of FIG. 14.

For each AW placeholder, one or more attributes such as study category, modality, series description, 3D applications, etc., can be applied to hanging criteria for the AW placeholder. Note that adding more attributes can result in more narrow matching. To modify the hanging criteria, a user can simply right click on the criteria, for example.

In certain examples, when a study is being launched, a matching layout (e.g., defined in Layout Editor settings) with a predefined hanging protocol can be applied (e.g., first in the available hanging protocol list). If an AW 3D placeholder is defined in this hanging protocol, and all matching criteria matches, the AW 3D application can be automatically launched within that placeholder.

Figure 15:
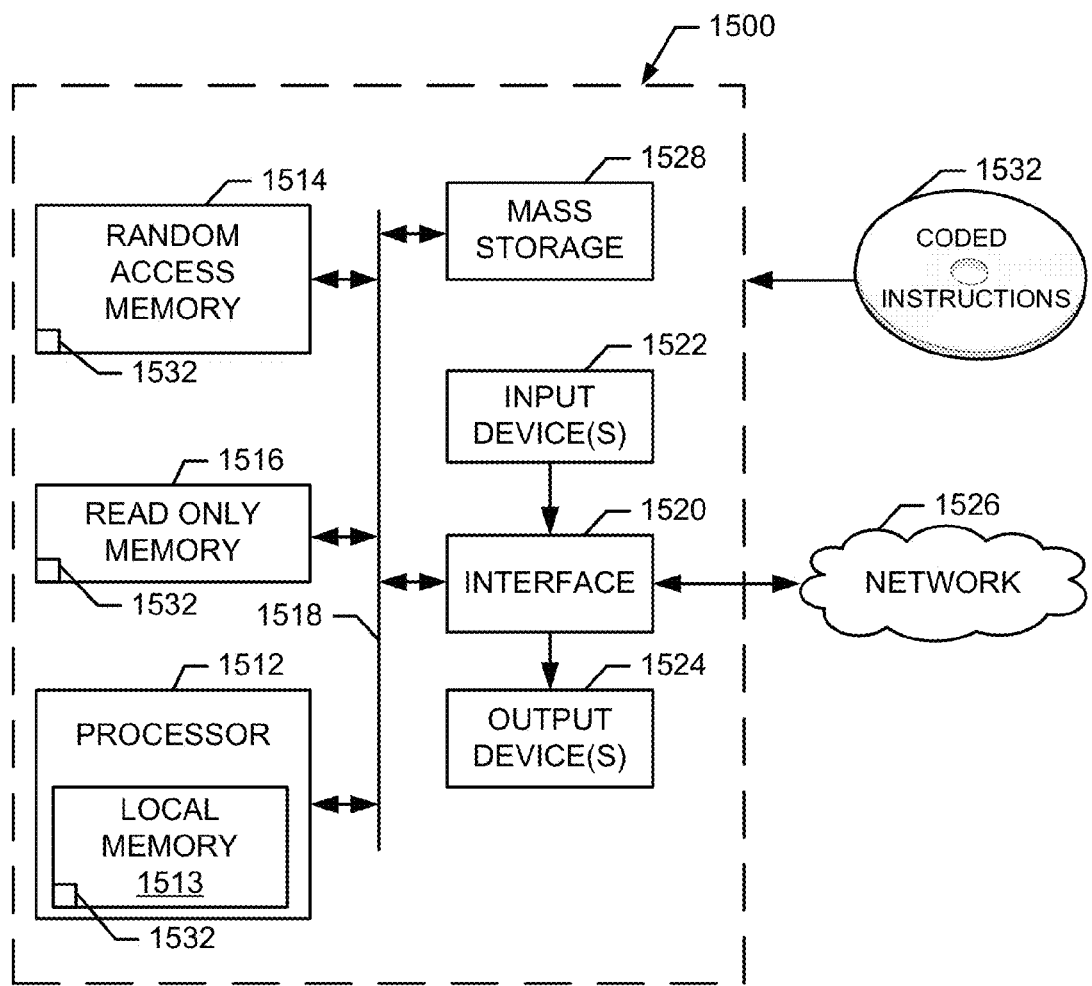
FIG. 15 is a block diagram of an example processor platform that may be used to execute the instructions of FIGS. 8-12 to implement the example IW viewer of FIG. 5, the example application and messaging integrator of FIG. 6, the example AW client of FIG. 7, and/or, more generally, the example integration system of FIG. 4.

FIG. 15 is a block diagram of an example processor platform 1500 capable of executing the instructions of FIGS. 8, 9, 10, 11, and/or 12 to implement the example IW viewer 402 of FIG. 5, the example application and messaging integrator 404 of FIG. 6, the example AW client 406 of FIG. 7, and/or, more generally, the example integration system 400 of FIG. 4. The processor platform 1500 can be, for example, a server, a personal computer, an Internet appliance, a set top box, or any other type of computing device.

The processor platform 1500 of the instant example includes a processor 1512. For example, the processor 1512 can be implemented by one or more microprocessors or controllers from any desired family or manufacturer. The processor 1512 includes a local memory 1513 (e.g., a cache) and is in communication with a main memory including a volatile memory 1514 and a non-volatile memory 1516 via a bus 1518. The volatile memory 1514 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1516 may be implemented by flash memory and/or any other desired type of memory device. Access to the main memory 1514, 1516 is controlled by a memory controller.

The processor platform 1500 also includes an interface circuit 1520. The interface circuit 1520 may be implemented by any type of interface standard, such as an Ethernet interface, a universal serial bus (USB), and/or a PCI express interface.

One or more input devices 1522 are connected to the interface circuit 1520. The input device(s) 1522 permit a user to enter data and commands into the processor 1512. The input device(s) can be implemented by, for example, a keyboard, a mouse, a touchscreen, a track-pad, a trackball, isopoint and/or a voice recognition system.

One or more output devices 1524 are also connected to the interface circuit 1520. The output devices 1524 can be implemented, for example, by display devices (e.g., a liquid crystal display, a cathode ray tube display (CRT), etc.). The interface circuit 1520, thus, typically includes a graphics driver card.

The interface circuit 1520 also includes a communication device such as a modem or network interface card to facilitate exchange of data with external computers via a network 1526 (e.g., an Ethernet connection, a digital subscriber line (DSL), a telephone line, coaxial cable, a cellular telephone system, etc.).

The processor platform 1500 also includes one or more mass storage devices 1528 for storing software and data. Examples of such mass storage devices 1528 include floppy disk drives, hard drive disks, compact disk drives and digital versatile disk (DVD) drives. The mass storage device 1528 may implement a local storage device.

The coded instructions 1532 of FIGS. 8, 9, 10, 11, and/or 12 may be stored in the mass storage device 1528, in the volatile memory 1514, in the non-volatile memory 1516, and/or on a removable storage medium such as a CD or DVD.

Although certain example methods, systems, apparatus, and articles of manufacture have been described herein, the scope of coverage of this patent is not limited thereto. On the contrary, this patent covers all methods, systems and articles of manufacture fairly falling within the scope of the claims of this patent.

What is claimed is:

1. A method for clinical application integration, said method comprising:
   creating, by a first clinical viewer, an application and messaging integrator to initiate an integrated interface associated with the first clinical viewer;
   starting, by the application and messaging integrator, a second clinical viewer by sending a launch message, the launch message comprising an instance identifier, an application identifier, and a study identifier for creating a window of the second clinical viewer in the integrated interface;
   associating the second clinical viewer with the integrated interface via the application and messaging integrator, the application and messaging integrator being created to facilitate communication between the first and second clinical viewers such that a single message loop is used to share messages between the first clinical viewer and the second clinical viewer in a shared context;
   sending, by the second clinical viewer upon successful startup, a notification message to the first clinical viewer via the single message loop of the application and messaging integrator, the notification message instructing the first clinical viewer to create a window of the first clinical viewer in the integrated interface, wherein the first clinical viewer and the second clinical viewer are re-parented to integrate the first and second clinical viewers into a single application view in the integrated interface;
   receiving a user input via the integrated interface;
   sending a message based on the user input to the first clinical viewer and the second clinical viewer via the application and messaging integrator;
   updating information at the second clinical viewer based on the message via the single message loop of the application and messaging integrator;
   and displaying the updated information at the second clinical viewer via the integrated interface.

2. The method of claim 1, wherein the application and messaging integrator is created by the first clinical viewer.

3. The method of claim 1, further comprising determining if the first clinical viewer is connected to the second clinical viewer via the application and messaging integrator.

4. The method of claim 1, further comprising launching an application containing the updated information at the second clinical viewer via the integrated interface based on the message received from the first clinical viewer.

5. The method of claim 1, wherein the integrated interface includes options from both a first clinical viewer interface and a second clinical viewer interface integrated into the integrated interface.

6. The method of claim 5, wherein the integrated interface allows the user to access all available options of both the first clinical viewer and the second clinical viewer.

7. The method of claim 1, wherein the method is implemented using a tangible computer-readable medium including instructions that, when executed, cause a computing device to at least:
   spawn, by a first clinical viewer, an application and messaging integrator to initiate an integrated interface associated with the first clinical viewer;
   start, by the application and messaging integrator, a second clinical viewer;
   associate the second clinical viewer with the integrated interface via the application and messaging integrator;
   receive a user input via the integrated interface;
   send a message based on the user input to the first clinical viewer and the second clinical viewer via the application and messaging integrator, the integrated interface providing a single application view for the first clinical viewer and the second clinical viewer, and the application and messaging integrator being created to facilitate communication between the first and second clinical viewers such that a single message loop is used to share messages between the first clinical viewer and the second clinical viewer in a shared context;
   update information at the second clinical viewer based on the message via the single message loop of the application and messaging integrator; and
   display the updated information at the second clinical viewer via the integrated interface.

8. A method for clinical application integration, said method comprising:
   instantiating, by a first clinical viewer, an application and messaging integrator to facilitate communication between the first clinical viewer and a second clinical viewer such that a single message loop is used to share messages between the first clinical viewer and the second clinical viewer in a shared context, the integrated interface providing a single application view for the first clinical viewer and the second clinical viewer and including options from both a first clinical viewer interface and a second clinical viewer interface integrated into the single integrated interface;

starting, by the application and messaging integrator, a second clinical viewer by sending a launch message, the launch message comprising an instance identifier, an application identifier, and a study identifier for creating a window of the second clinical viewer in the integrated interface;

associating the second clinical viewer with the integrated interface via the application and messaging integrator;

sending, by the second clinical viewer upon successful startup, a notification message to the first clinical viewer via the single message loop of the application and messaging integrator, the notification message instructing the first clinical viewer to create a window of the first clinical viewer in the integrated interface, wherein the first clinical viewer and the second clinical viewer are re-parented to integrate the first and second clinical viewers into the single application view in the integrated interface;

receiving a user input via the single integrated interface;

operating on the user input via the first clinical viewer;

and sharing the user input with the second clinical viewer by sending a message based on the user input to the second clinical viewer via the single message loop of the application and messaging integrator.

9. The method of claim 8, further comprising determining if the first clinical viewer is connected to the second clinical viewer via the application and messaging integrator.

10. The method of claim 8, wherein the method is implemented using a tangible computer-readable medium including instructions that, when executed, cause a computing device to at least:

instantiate, by a first clinical viewer, an application and messaging integrator to facilitate communication between the first clinical viewer and a second clinical viewer such that a single message loop is used to share messages between the first clinical viewer and the second clinical viewer in a shared context, wherein a single integrated interface is provided to access the first and second clinical viewers and wherein the second clinical viewer is launched by the application and messaging integrator, the integrated interface providing a single application view for the first clinical viewer and the second clinical viewer and including options from both a first clinical viewer interface and a second clinical viewer interface integrated into the single integrated interface, wherein the first clinical viewer and the second clinical viewer are re-parented to integrate the first and second clinical viewers into the single application view in the single integrated interface;

receive a user input via the single integrated interface;

operate on the user input via the first clinical viewer; and share the user input with the second clinical viewer by sending the message based on the user input to the second clinical viewer via the single message loop of the application and messaging integrator.

11. A system for clinical application integration, said system comprising:

a first clinical viewer;

an application and messaging integrator, created by the first clinical viewer, to initiate an integrated interface with a second clinical viewer; and a processor coupled to memory configured to perform actions comprising:

starting, by the application and messaging integrator, the second clinical viewer by sending a launch message, the launch message comprising an instance identifier, an application identifier, and a study identifier for creating a window of the second clinical viewer in the integrated interface;

associating the second clinical viewer with the integrated interface via the application and messaging integrator, the application and messaging integrator being created to facilitate communication between the first and second clinical viewers such that a single message loop is used to share messages between the first clinical viewer and the second clinical viewer in a shared context;

sending, by the second clinical viewer upon successful startup, a notification message to the first clinical viewer via the single message loop of the application and messaging integrator, the notification message instructing the first clinical viewer to create a window of the first clinical viewer in the integrated interface, wherein the first clinical viewer and the second clinical viewer are re-parented to integrate the first and second clinical viewers into a single application view in the integrated interface;

sending a message based on a user input received via the integrated interface to the first clinical viewer and the second clinical viewer via the application and messaging integrator, the second clinical viewer to receive the message and update information based on the message via the single message loop of the application and messaging integrator, wherein the updated information is displayed at the second clinical viewer via the integrated interface.

12. The system of claim 11, wherein the first clinical viewer determines if the first clinical viewer is connected to the second clinical viewer via the application and messaging integrator.

13. The system of claim 11, wherein the second clinical viewer launches an application containing the updated information via the integrated interface based on the message received from the first clinical viewer.

14. The system of claim 11, wherein the integrated interface includes options from both a first clinical viewer interface and a second clinical viewer interface integrated into the integrated interface.

15. A system for clinical application integration, said system comprising:

a first clinical viewer to:

instantiate an application and messaging integrator to facilitate communication between the first clinical viewer and a second clinical viewer such that a single message loop is used to share messages between the first clinical viewer and the second clinical viewer in a shared context, the integrated interface providing a single application view for the first clinical viewer and the second clinical viewer and including options from both a first clinical viewer interface and a second clinical viewer interface integrated into the single integrated interface; and a processor coupled to memory configured to:

start, by the application and messaging integrator, a second clinical viewer by sending a launch message, the launch message comprising an instance identifier, an application identifier, and a study identifier for creating a window of the second clinical viewer in the integrated interface;

associate the second clinical viewer with the integrated interface via the application and messaging integrator;

send, by the second clinical viewer upon successful startup, a notification message to the first clinical viewer via the single message loop of the application and messaging integrator, the notification message instructing the first clinical viewer to create a window of the first clinical viewer in the integrated interface, wherein the first clinical viewer and the second clinical viewer are re-parented to integrate the first and second clinical viewers into the single application view in the integrated interface;

receive a user input via the single integrated interface;

operate on the user input; and share the user input with the second clinical viewer by sending a message based on the user input to the second clinical viewer via the single message loop of the application and messaging integrator.

16. The system of claim 15, wherein the first clinical viewer determines if the first clinical viewer is connected to the second clinical viewer via the application and messaging integrator.

* * * * *